United States Patent
Lange et al.

(10) Patent No.: US 9,561,058 B2
(45) Date of Patent: Feb. 7, 2017

(54) ILIAC CONNECTOR, CONNECTOR HEAD, SPINAL FIXATION SYSTEM AND METHOD OF STABILIZING A SPINE

(71) Applicant: coLigne AG, Zürich (CH)

(72) Inventors: Robert Lange, Paris (FR); Jakob Funnemark, Zürich (CH); Paul Fayada, St. Georges (FR); Vittoria Brighenti, Zollikon (CH)

(73) Assignee: COLIGNE AG, Zurich (CH)

( * ) Notice: Subject to any disclaimer, the term of this patent is extended or adjusted under 35 U.S.C. 154(b) by 68 days.

(21) Appl. No.: 13/890,822

(22) Filed: May 9, 2013

(65) Prior Publication Data

US 2013/0304128 A1  Nov. 14, 2013

Related U.S. Application Data

(60) Provisional application No. 61/644,689, filed on May 9, 2012.

(51) Int. Cl.
*A61B 17/70* (2006.01)

(52) U.S. Cl.
CPC ......... *A61B 17/705* (2013.01); *A61B 17/7001* (2013.01); *A61B 17/7031* (2013.01); *A61B 17/7055* (2013.01); *A61B 17/7032* (2013.01)

(58) Field of Classification Search
CPC .......................... A61B 17/705; A61B 17/7055
USPC .................................................. 606/246–278
See application file for complete search history.

(56) References Cited

U.S. PATENT DOCUMENTS

| | | | |
|---|---|---|---|
| 5,133,717 A | | 7/1992 | Chopin |
| 5,374,267 A | * | 12/1994 | Siegal .......................... 606/250 |
| 5,593,407 A | | 1/1997 | Reis |
| 2003/0032959 A1 | * | 2/2003 | Yeh ................................ 606/61 |
| 2005/0101956 A1 | * | 5/2005 | Simonson ....................... 606/61 |
| 2005/0228378 A1 | * | 10/2005 | Kalfas et al. ................... 606/61 |
| 2005/0277932 A1 | | 12/2005 | Farris et al. |
| 2005/0288669 A1 | * | 12/2005 | Abdou ............................ 606/61 |
| 2006/0058789 A1 | * | 3/2006 | Kim et al. ...................... 606/61 |
| 2006/0206114 A1 | * | 9/2006 | Ensign et al. .................. 606/61 |
| 2006/0229611 A1 | * | 10/2006 | Avery et al. ................... 606/61 |

(Continued)

FOREIGN PATENT DOCUMENTS

| | | |
|---|---|---|
| EP | 1238637 A1 | 9/2002 |
| JP | 3091440 B2 | 9/2000 |
| JP | H11244299 A | 9/2002 |

OTHER PUBLICATIONS

CFR PEEK Composite for Surgical Applications, Medical Plastics, Jan. 1, 2007, by Stuart Green, PhD ("Green").*

(Continued)

*Primary Examiner* — Ellen C Hammond
*Assistant Examiner* — Stuart S Bray
(74) *Attorney, Agent, or Firm* — Browdy and Neimark, PLLC (57) ABSTRACT

An inventive iliac connector comprises a connector head (1) and a connecting rod (2) for connecting a sacrum (S) or a spine (SP) to an ilium (I). The connector head (1) has a first hole (15) for holding a spinal rod (3) and a second hole (16) for holding the connecting rod (2), wherein the connecting rod (2) is made of a material being more flexible than titanium. This iliac connector enables a stabilization of ilium, sacrum and spine and enables at the same time movement between ilium and sacrum.

28 Claims, 7 Drawing Sheets

(56) References Cited

U.S. PATENT DOCUMENTS

| | | | |
|---|---|---|---|
| 2006/0233597 A1* | 10/2006 | Ensign et al. | 403/177 |
| 2007/0118121 A1* | 5/2007 | Purcell et al. | 606/61 |
| 2007/0173825 A1* | 7/2007 | Sharifi-Mehr et al. | 606/61 |
| 2007/0191846 A1* | 8/2007 | Bruneau et al. | 606/61 |
| 2007/0270816 A1* | 11/2007 | Rezach | 606/61 |
| 2008/0021454 A1* | 1/2008 | Chao et al. | 606/61 |
| 2008/0021455 A1* | 1/2008 | Chao et al. | 606/61 |
| 2008/0021456 A1* | 1/2008 | Gupta et al. | 606/61 |
| 2008/0058805 A1* | 3/2008 | Stuart | 606/61 |
| 2008/0082112 A1* | 4/2008 | Lawton et al. | 606/151 |
| 2008/0215095 A1 | 9/2008 | Biedermann et al. | |
| 2008/0234743 A1* | 9/2008 | Marik | 606/257 |
| 2008/0255617 A1* | 10/2008 | Cho et al. | 606/246 |
| 2008/0262553 A1* | 10/2008 | Hawkins et al. | 606/278 |
| 2008/0281362 A1* | 11/2008 | Lemoine | 606/261 |
| 2009/0204156 A1* | 8/2009 | McClintock et al. | 606/278 |
| 2009/0259256 A1* | 10/2009 | Miller | 606/250 |
| 2009/0281573 A1* | 11/2009 | Biedermann et al. | 606/257 |
| 2010/0087864 A1* | 4/2010 | Klein et al. | 606/264 |
| 2010/0137913 A1* | 6/2010 | Khatchadourian et al. | 606/258 |
| 2010/0280552 A1* | 11/2010 | Lee | 606/250 |
| 2010/0298884 A1* | 11/2010 | Faizan et al. | 606/266 |
| 2011/0087287 A1* | 4/2011 | Reeder et al. | 606/250 |
| 2011/0118786 A1* | 5/2011 | Jang | 606/264 |
| 2011/0282391 A1* | 11/2011 | Dall | 606/278 |
| 2012/0022595 A1 | 1/2012 | Pham et al. | |
| 2012/0029567 A1* | 2/2012 | Zolotov et al. | 606/264 |
| 2012/0029571 A1* | 2/2012 | Schwab et al. | 606/278 |
| 2012/0078306 A1* | 3/2012 | Lynch | 606/264 |
| 2012/0109210 A1* | 5/2012 | Baker et al. | 606/264 |
| 2012/0179205 A1* | 7/2012 | Miller | 606/264 |
| 2013/0006307 A1* | 1/2013 | Robinson et al. | 606/252 |
| 2013/0123850 A1* | 5/2013 | Schoenefeld et al. | 606/248 |
| 2013/0123851 A1* | 5/2013 | Seme et al. | 606/250 |
| 2013/0211457 A1* | 8/2013 | Dickinson et al. | 606/264 |
| 2013/0274808 A1* | 10/2013 | Larroque-Lahitette et al. | 606/278 |
| 2014/0214083 A1* | 7/2014 | Refai et al. | 606/256 |
| 2014/0257396 A1* | 9/2014 | Powers et al. | 606/259 |
| 2014/0303674 A1* | 10/2014 | Sasing | 606/278 |

OTHER PUBLICATIONS

Flexible Rods and the Case for Dynamic Stabilization, in Neurosurg Focus. 2007;22(1), Jason M. Highsmith et al.*
European Search Report of EP13166637 dated Jan. 13, 2014.

* cited by examiner

FIG. 20

ILIAC CONNECTOR, CONNECTOR HEAD, SPINAL FIXATION SYSTEM AND METHOD OF STABILIZING A SPINE

This patent application claims priority of U.S. provisional application No. 61/644,689 filed on May 9, 2012. The present invention is in the field of stabilization and fixation of a spine.

TECHNICAL FIELD

Prior Art

Several fixation techniques are known for the treatment of spinal deformities and pathologies, among them spinal fusion. While this is an extensive operation with potentially serious complications, a spinal fusion can be considered a lesser evil than the problem the surgeon must solve. The diseased spinal segments of a patient may be so unstable, painful and potentially nerve damaging that blocking mobile spine segments to form one bone is thought to be the best method of treatment. To fix the spine, surgeons attach one or more longitudinal fixation elements, such as rods or plates, to the spine at several fixation sites using bone screws. Often spinal bone screws are fixed through one of the most solid sections of a vertebrae, the pedicle.

The vertebral pedicles connect the anterior vertebral body to its posterior elements where the actuating back muscles are attached. The pedicles at each motion segment work like a lever between the back and the front of the spine. They mediate almost all the forces from the back muscles to the anterior spine, enabling the human being to stand erect and to bend forward in a controlled manner. From the cervical to the lumbar spine that stops adjacent to the sacrum, the pedicle is the most solid structure to place a screw that is connected by a longitudinal element that fixes motion segments of the spine.

EP 1 238 637 discloses a well-working longitudinal implant fastened on bones on either side of a damaged area of the spine. Pedicle bone screws are used for the fixation. The longitudinal implant is a carbon filament composite material, wherein the filament is encapsulated in a polymer matrix. The material is known on the market as ostaPek.

Sometimes, a surgeon must extend a long fusion beyond the lumbar spine and connect it to the sacrum where the bone is soft and spongy. At end of a long fusion construct, the implant forms a long lever arm that works to pull the screws from this soft sacral bone.

To prevent a screw pull-out from the sacrum and a fusion-construct failure, it is known to increase the anchor locations. This can be done with multiple screws in the sacrum. It is also known to extend the entire construct lateral, crossing the sacral iliac joint to engage the iliac bone as well.

U.S. Pat. No. 5,133,717 shows a sacral support saddle for fastening a spinal rod to the sacrum.

U.S. Pat. No. 5,593,407 suggests to connect the lowest lumbar vertebra directly to the ilium, using a bent rod and pedicle screws.

US 2012/0022595 describes a sacral-iliac stabilization system with a sacral-iliac plate having a first screw hole for receiving a first fastener to secure the iliac portion to the iliac bone. A second and third screw hole is also provided for receiving a second and a third fastener to secure the sacral portion to the sacral bone. US 2006/0106382 also discloses a plate connecting the sacrum to the ilium. US 2008/0154306 suggests using long screws to connect the sacrum to the ilium.

US 2008/0021456 shows a quite complicated system comprising a plate on the ilium, rod like connectors to the sacrum and a stabilization plate between the lowest lumbar vertebra and the sacrum.

US 2008/0021455 discloses a sacral-iliac cross connector to allow for coupling of the connector to a spinal fixation rod and anchors. The connector has a receiver head with opposed sidewalls defining a seating portion for an insert which is configured to seat a spinal rod. The connector also includes a connecting rod with a flat end part comprising a hole. This end part is held in a slot on the bottom side of the seating portion and it is fixed to a post or shaft arranged on the bottom side of the insert. Therefore, the connecting rod has to be arranged and fixed before the spinal rod can be placed into the insert and fixed therein.

US 2008/0021454, which refers to US 2008/0021455, shows in FIG. 5A a spine fixation system with a spinal rod, a sacral-iliac cross connector comprising a connector rod and a plate fixed on the ilium.

However, the loss of the sacral-iliac joint is very much noticed by the patient when blocked. The reason for this is the following:

The pelvis comprises three bony parts (two iliac bones and the sacrum). Together the iliac bones and sacrum form a ring, with the iliac bones joined anterior at the pubis and the sacrum placed posterior between iliac bones like a keystone. The pelvic ring is held together by a multitude of complex ligaments. These ligaments allow small movement, particularly at the sacro-iliac joints, that are paired left and right between the sacrum and the pelvis. With their ligaments, the sacral-iliac joints allow a subtle nodding movement of the sacrum between the iliac bones at all changes in posture. This slightly changes the form of the pelvic ring during forward bending (flexion) and backward bending (extension). In this manner, this subtle sacral movement and change in pelvic form become a mechanism that absorbs energy propagated from the limbs to the spine and vice versa. This mechanism is often unnoticed by the patient until it is disrupted or gone.

Sacral-iliac fixations, designed to prevent screw pull out from the sacrum, also eliminate the ability of the sacral-iliac joint to gently flex and nod in a normal manner, which allow certain postures and energy absorption between the lower and upper body. Since the posterior ligaments are removed and the joint blocked, a minute, but yet significant motion is lost. All energy is driven into the spine from the pelvis and sacrum that has become one bone. Shocks can not be absorbed correctly. Shocks are uncomfortable and over time can degenerate the surrounding joints of the hips and spine.

SUMMARY OF THE INVENTION

It is therefore an object of the invention to allow a stabilization of the iliac area while still enabling a natural movement between ilium and sacrum.

The inventive iliac connector comprises a connector head and an elongate connecting member for connecting a sacrum or a spine to an ilium. The connector head has a first hole for holding an elongate spinal member and a second hole for holding the elongate connecting member, wherein the elongate connecting member is made of a material being more flexible than titanium. Preferably, the elongate connecting member is made of a material less flexible than a rope or a rubber band.

At least one of the elongate connecting member and the elongate spinal member, preferably both, are rods. In the following the expression "rod" will be use, wherein other shapes are meant as well.

Since the connecting rod is more flexible than titanium, movement of the ilium relative to the sacrum is still possible. However the rod gives sufficient stabilization between these two parts. The rod allows a very low deformation in longitudinal direction but still allows sufficient bending and rotation around its longitudinal direction. It also allows, when coupled with a spinal rod a coupled motion.

This spinal fixation system applies a corrective force upon the spine, but does also allow some deflection, returning resiliently due to the inherent memory of form that is desired by the surgeon as the patient moves and as normal body stress are exerted upon it. This spinal fixation system is elastic enough to allow stress to pass through adjacent and connected bones that will encourage bone growth and then return to the original corrective form while at the same time it is not so flexible as to over stress the bone and cause micro stress fractures.

The rod can be straight or curved in its initial position without any force applied to it.

In a preferred embodiment, the connecting rod is made of a filament composite material, preferably with long strands or filaments. Preferably the filaments are carbon filaments. The filaments are preferably oriented, thereby extending mainly in longitudinal direction of the connecting rod. Preferably, the filaments are woven. A matrix preferably holds the carbon strands in place when load passes through the carbon fibers, while at the same time, allows some matrix stretching between the fibers. This brings flexibility and spring-like qualities to the rod in bending as well as torsion. Preferably, the connecting rod is a composite rod as described in EP 1 238 637.

The rod can have the same fiber orientation and matrix arrangement throughout the whole length of the connecting rod. However the connecting rod can also have different orientation of the fibers at different locations in the rod to make it stronger, stiffer or more flexible at these different locations. A disclosure of such a rod can be found in US 2008/026548.

In a preferred embodiment, the carbon filaments are encapsulated in a polymer matrix, the matrix being preferably polyether-ketoneetherketoneketone (PEKEKK) or polyetheretherketone (PEEK).

In a preferred embodiment, the connecting rod has throughout its whole length a non-changing outer geometry, even when the stiffness of the rod changes throughout its length. Preferably, the rod has a round cross-section. It can also have other shapes, such as a polygonal cross-section. This simplifies production as well as surgery, since the rod can be manufactured in standard lengths and it can be cut for each application individually.

It is a further advantage of the inventive iliac connector that the rod is made of a radio lucent material. This enables the surgeon to analyze tissue and bone beneath the iliac connector, to observe bone formation or detect other pathologies at a later time.

The invention also refers to a special connector head, which can for example be used in the inventive iliac connector. This connector head has a first hole defining a first central axis for holding a spinal rod and a second hole defining a central second axis for holding a connecting rod, the two central axes extending in different directions and at a distance to each other. Each hole is in communication with a separate fixation opening, the fixation openings being arranged such they allow mounting of the connecting rod and the spinal rod independently from each other. This connector head can hold two rods, i.e. a spinal rod and a connecting rod, individually. It does not depend which one is fixed first within the connector head. An already fixed rod can also made loose again without manipulation of the other rod. The surgeon has therefore utmost ability to adapt the fixation to the local anatomy and to the goals for treatment. For example, the two rods can be placed in any order, secured in any sequence that is optimal for precision in placement, for the ease of assembly and to place progressive forces to better align the spine This connector head is preferably used with this stiff and flexible rod mentioned above. However it can also be used with other rods, for example rods known in the state of the art which are used for spinal corrections. It can also be used for combining to other kind of rods, not only as iliac connector.

Preferably, the first central axis of the first hole and the second central axis of the second hole extend in two planes extending at a distance from each other but parallel to each other. However, it is also possible that these two planes are arranged in an angle to each other, i.e. one of the holes being tilted with respect to the other hole.

In a preferred embodiment, the fixation opening of the first hole is arranged at an angle α different from 90° to the fixation opening of the second hole. This makes both fixation openings easily accessible for the surgeon. Preferred angles are between 70° to 30°, more preferably between 60° to 40°. In one example the angle α is about 60°. In preferred embodiments the angle α is about 45° or less. In another preferred embodiment, this angle is approximately 0°.

The connector head preferably comprises two side walls, a rear wall, a front wall, a bottom and a top, wherein the first hole is arranged in one of the side walls, the second hole is arranged in the rear wall, the first fixation opening is arranged in the front wall and the second fixation opening is arranged in the top. This arrangement allows minimizing the size of the connector head. Preferably, the back wall is perpendicular to the side walls and the top is perpendicular to the rear wall and the side walls. The side walls can be parallel to each other. Preferably, the edges between the walls are rounded.

In a preferred embodiment, the front wall comprises at least one section which is inclined with respect to the rear wall. The first fixation opening is arranged in the inclined section. This minimizes the size of the connector head even more and allows a good access to the fixation openings.

The size is further minimized and optimized to local conditions when a transition area connecting the back wall and the bottom has a rounded outer shape.

Preferably, at least some, preferably all of the following walls are plane: the side walls, the rear wall, the front wall and the top.

In another preferred embodiment of the connector head, the first fixation opening is arranged in a first surface of the connector head and the second fixation opening is arranged in a second surface of the connector head, wherein the first surface extends in a plane parallel but at a distance to a plane defined by the second surface. This allows a good access to the fixation openings and places the head further away from the skin to create a less prominent implant construct.

Access and size are also optimized when the connector head comprises a first body with a cube-like shape and a second body with a cube-like shape, the first body comprising the first hole and the first fixation opening and the second body comprising the second hole and the second fixation opening, wherein the first body is arranged staggered below the second body.

A connector head comprising the features of both paragraphs mentioned above has been found to be a preferred embodiment.

The first and second holes can be blind holes. Preferably, at least one and most preferably both of them are straight through holes. The first hole preferably extends from a first of the side walls to a second of the side walls and the second hole extends from the rear wall to the front wall. The spinal rod and the connecting rod can therefore penetrate the connector head and the surgeon has during operation utmost ability to define the length of the clamped parts of the rods, the rods being clamped between connector head and the anchors, for example the pedicle bone screws.

Preferably, the spinal rod and/or the connecting rod are firmly, i.e. fixedly held in the connector head. Preferably, both of them are firmly held within the connector heads, not allowing any lateral, longitudinal or rotational rod movement at their fixation points.

The above mentioned connector is preferably used in a spinal fixation system, wherein this system further comprises a spinal rod made of a material being more flexible than titanium, spinal bone screws and preferably at least one sacral bone screw being penetrated by this spinal rod. The spinal rod is hold in the iliac connector head. At least one iliac bone screw can be present fixed in the ilium, wherein the connecting rod of the iliac connector is held in the at least one iliac bone screw. Preferably, the spinal rod and the connecting rod are made of the same material, especially the one described above. This system allows the stabilization of the spine and the ilium thereby allowing some movement between ilium and sacrum.

Preferably the system uses fixation screws into the sacrum as well, therefore fixing the spinal rod to the sacrum and connecting the sacrum with the ilium using the inventive iliac connector. However it is also possible to connect the lowest lumbar vertebra directly to the ilium by using the inventive connector.

The inventive system maintains some movement at the sacral-iliac joint by placing spinal rod and connecting rod at an angle to each other, preferably almost perpendicular to one another, wherein at least the connecting rod is made of a material being more flexible than titanium. Preferably, the rods are made of a composite material comprising fibres oriented in longitudinal direction of the rod, so that the fibres of the different rods are oriented at an angle, preferably about 90° to each other, for example 84°.

The connecting rod works in rotation and with some bending making a coupled movement, while the spinal rod preferably works in flexion and extension as well as some torsion of the spine. This system more closely approximates the function of the posterior sacral-iliac ligaments, while at the same time preventing pull out of the screws at the sacrum. It also absorbs shocks better by allowing a minute but significant movement of the sacrum between the iliac bones of the pelvis during flexion (forward bending) and extension (backward bending). In addition stress shielding and the possible consequence of osteoporosis is avoided in the pelvis and sacrum.

This system is more comfortable for the patient; it protects the surrounding hips and spine that are adjacent to the fusion construct, and prevents screw pull out and construct failure at the sacrum.

The inventive method for stabilizing a spine comprises the steps of a) accessing the sacrum and iliac portions of the spine;
b) fixing an elongate spinal member with at least one spinal bone screw to at least one pedicle of the spine, the elongate spinal member having a first end;
c) fixing an elongate connecting member with a iliac bone screw to the iliac, the elongate connecting member having a second end and
d) fixing the first end of the elongate spinal member and the second end of the elongate connecting member relative to each other at an angle of about 90°, wherein the chronology of fixation of the first end the second end can be chosen by the surgeon.

In a preferred variant, the method further comprises the step of fixing the elongate spinal member with at least one, preferably exactly one sacral bone screw to the sacrum and providing a sacral-iliac connection between ilium and sacrum by fixing the first end of the elongate spinal member and the second end of the elongate connecting member relative to each other.

Fixation of the two ends is preferably established with a connector head comprising two holes into which the two ends are introduced and fixed. Preferably they are introduced separately and independently from each other and preferably, the fixation of each end is also independently from the other one.

This method enables the surgeon to choose or correct for example the placement of the iliac bone screw at a very late stage of the surgery after the longitudinal elements and pedicle screws have been placed in it is inter-operatively decided to extend the fusion. Also other parts of the spinal fixation system can be rearranged and their relationship to other parts can be changed within a small range at a late stage.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiment of the invention and not for the purpose of limiting the same. In the drawings is shown FIG. 1 a spinal fixation system according to a first embodiment of the invention fixed on a reconstruction of a human lower spine, sacrum and ilium.

DESCRIPTION OF PREFERRED EMBODIMENTS

Figure 1:
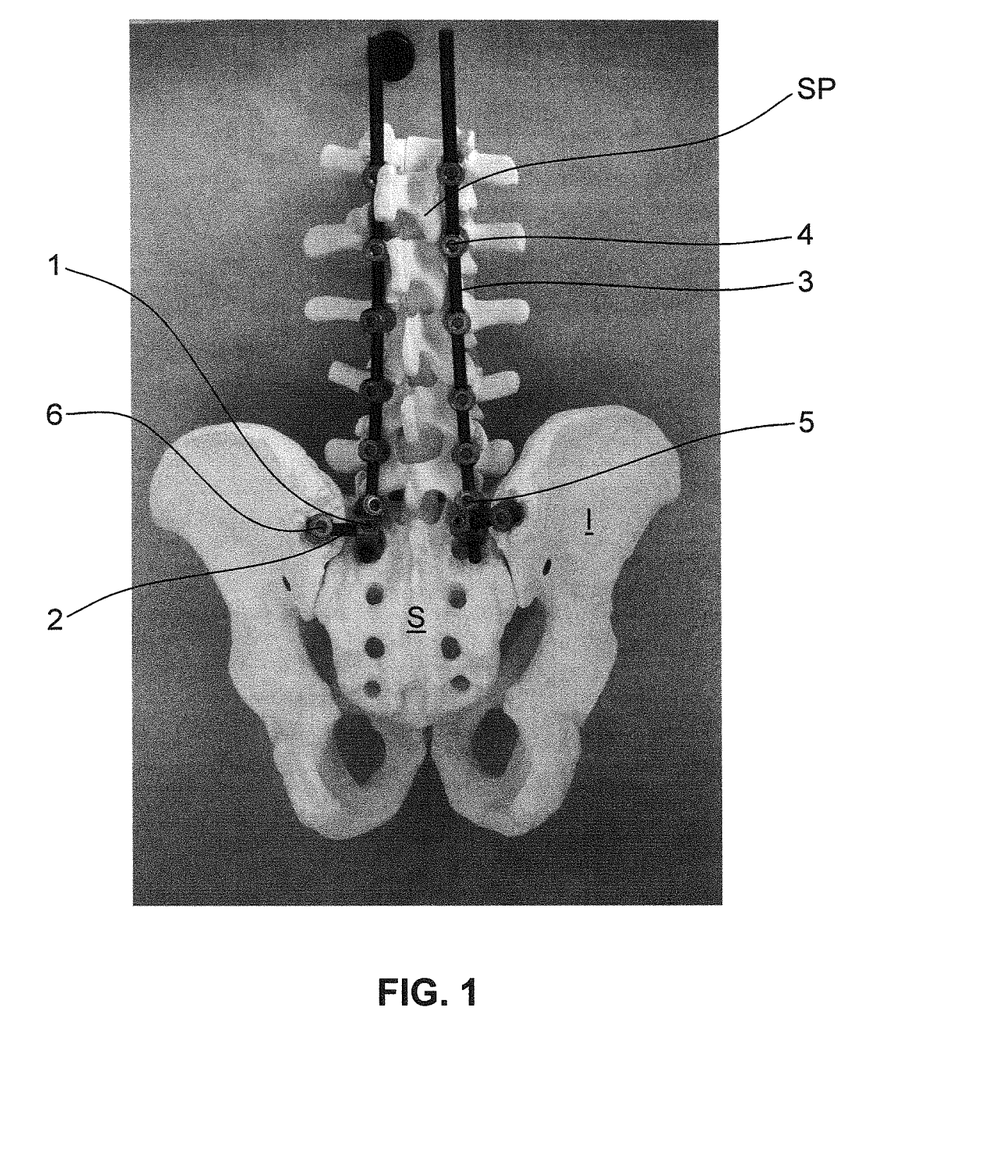
Figure 2:
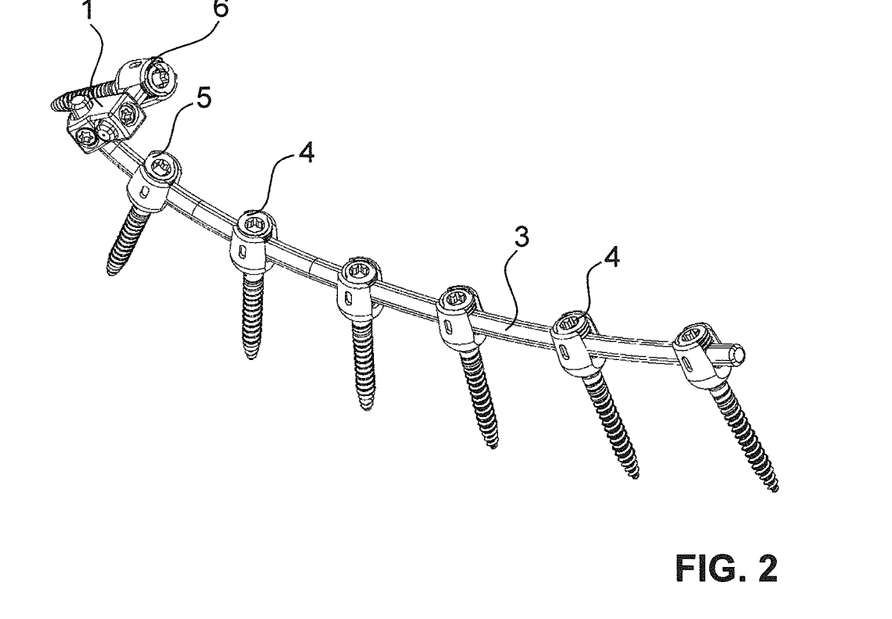
FIG. 2 the fixation system according to FIG. 1 in first perspective view.
Figure 3:
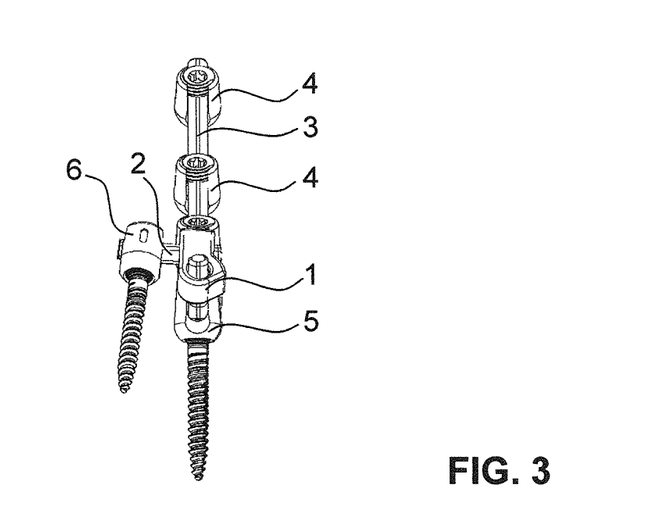
FIG. 3 the fixation system according to FIG. 1 in a second perspective view.

FIGS. 1 to 3 show a first embodiment of an inventive spinal fixation system using an inventive iliac connector and an inventive connector head.

The spinal fixation system comprises one preferably two spinal rods 3 extending along a spine SP and being fixed to one or more vertebrae of the spine SP. The spinal rod 3 is preferably curved. Known pedicle bone screws 4 are used as anchors for the fixation to the vertebrae, wherein these spinal bone screws 4 preferably have known tulip heads. The spinal bone screws 4 with the tulips are preferably made of titanium.

The spinal rod 3 is preferably made of a more flexible material, such as a filament composite material. Preferably it is made of carbon filaments encapsulated in a polymer matrix, such as PEKEKK or PEEK. The composite material preferably comprises of about 66.6% (weight %) of carbon fibers and of about 33.3% polyether-ketoneetherketoneketone (PEKEKK) as encapsulating matrix. The fibres or filaments are preferably oriented in layers which ar parallel to each other and to a surface of the rod. The layers may be made up of woven first and second filaments. The first filaments are oriented in an axial direction of the longitudinal rod. The second filaments are oriented to perpendicular to the axial direction. Such a material is known on the market with the name ostaPek of CoLigne AG and is described in EP 1 238 637 and US 2008/026548.

On one free end of the spinal rod 3, the last screw can be a sacral bone screw 5 fixed to the sacrum S. It can have, as shown in this example, the same shape and size as the spinal bone screws 4. However, it can also be different in size and/or in shape. The spinal rod 3 is penetrating the tulip of this sacral screw 5 as well. At the penetrating end of the spinal rod 3, a connector head 1 of an inventive iliac connector is arranged, wherein the spinal rod 3 preferably penetrates this connector head 1 as well before ending shortly thereafter.

The total length of the spinal rod 3 and the number of spinal bone screws 4 depend on the medical case.

Preferably, the connector head 1 is made of the same material as the screws. Preferably, it is made of titanium.

A connecting rod 2 is held within this connector head 1 extending at an angle from the spinal rod 3. This angle is preferably approximately 90°. The connecting rod 2 can be straight or curved as well. The connecting rod 2 is quite short. Preferably, its length is between 2 and 4 cm and more preferably about 3 cm.

The connecting rod 2 is made of a material which is more flexible than titanium. Preferably it is made of a filament composite material like the spinal rod 2 described above. Preferably, the spinal rod 3 and the connecting rod 2 of a common fixation structure are made of the same material, preferably the one described in EP 1 238 637 and US 2008/026548 and known in the market as ostPek of CoLigne AG.

The two rods 2, 3 can have the same outer geometry, especially the same diameter. Especially the connecting rod 2 has preferably a round cross-section and it has preferably throughout its length the same outer shape and the same diameter. Typical diameters are 4 to 8 mm, preferably about 6 mm. The connecting rod 2 can also have another cross-section, for example a polygonal one.

One free end of the connecting rod 2 penetrates the connector head 1. The other free end penetrates an anchor or fixation element which is fixed to the ilium I. Preferably, this fixation element is an iliac bone screw 6 as best seen in FIG. 3. This screw 6 preferably has a tulip as well. It can have the same shape and size as the sacral bone screw 5 and/or the spinal bone screw 4. However it also can have a different size and shape. Preferably, it is not combined with a plate and preferably it is only a single screw.

FIGS. 4 to 9 show the inventive connector head 1 in more detail. The connector head 1 has a generally cuboid main body wherein a transition area between two walls has a remarkably rounded shape and wherein an opposite wall to this transition area has an inclined section.

Figures 4, 5, 6, 7, 8:
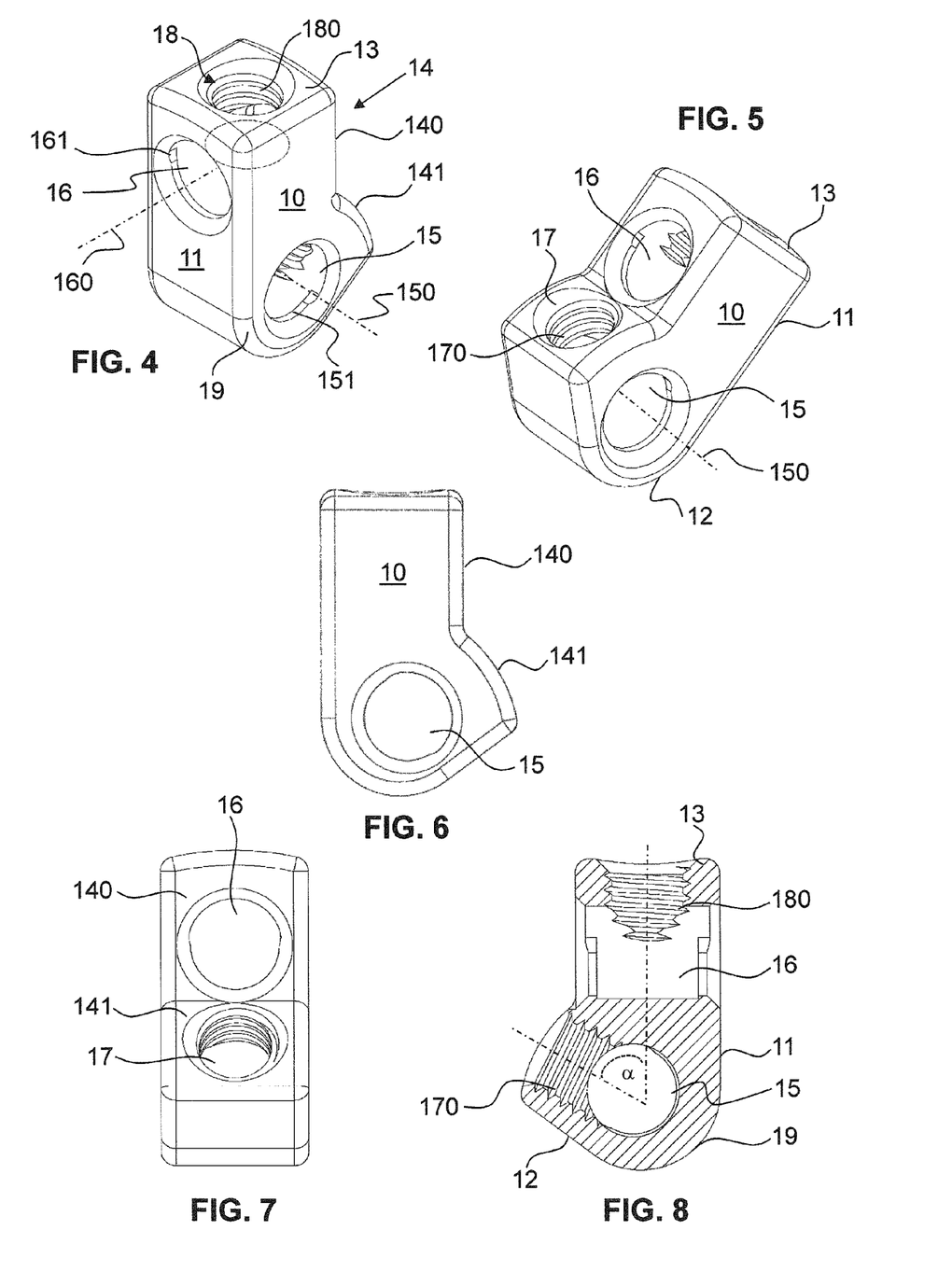
FIG. 4 a connector head according to the invention in a first perspective view.
FIG. 5 the connector head according to FIG. 4 in a second perspective view.
FIG. 6 a side view of the connector head according to FIG. 4.
FIG. 7 a front view of the connector head according to FIG. 4.
FIG. 8 a longitudinal section of the connector head according to FIG. 4.

As can be best seen in FIG. 4, the connector head comprises two opposite side walls 10, extending parallel to each other and being preferably plane. A plane rear wall 11 is arranged perpendicular to these side walls 10 and a flat top 13 is arranged perpendicular to the side walls 10 and the rear wall 11. A bottom 12 is inclined relative to the rear wall 11 and a front wall 14. Between the rear wall 11 and the bottom 12, the curved transition area 19 extends. The bottom 12 preferably has first the same curvature as the transition area 19, wherein it decreases continuously in direction to the front wall 14.

The front wall 14 has at least to sections: an upper flat section 140 extending perpendicular to the top 13 and the side walls 10 and therefore parallel to the rear wall 11 and a lower inclined section 141 extending to the bottom 12. The inclined section 141 is extending forward and increasing the width of the connector head 1 in direction to the bottom 12.

The directions used above, such as upper, lower, rear, front, bottom, top, refer to the orientation of the connector head 1 as shown in the FIGS. 4 to 8. They do not restrict that orientation of the connector head 1 when in use.

A first hole 15 is arranged in one of the side walls 10. Preferably, the first hole 15 is a through hole extending from one side wall 10 to the other. The first hole 15 has a first central axis 150 which extends perpendicular to the two side walls 10 from the first side wall to the second one.

The first hole 15 has at its two ends a slightly non-rounded shape, as can be best seen in FIG. 6 and FIG. 4 with reference number 151. This helps to fix the rod more securely within the hole. The rod is preferably the spinal rod 3.

In the front wall 14, in particular in the inclined lower section 141, a first fixation opening 17 is arranged, see FIG. 5. This first fixation opening 17 extends from the front wall 14 to the first hole 15 within the main body of the head 1, i.e. it crosses or leads into the first hole 15. This first fixation opening 17 comprises an internal thread, allowing a first fixation screw 171 (see FIG. 11) to be screwed into this opening 17.

A second hole 16 with a second central axis 160 extends from the rear wall 16 in direction to the front wall 14, in particular to the plane upper section 140. The second hole 16 is preferably a through hole as well, therefore ending in the front wall 14. This second hole 16 can have the same size and shape as the first hole 15. Preferably it has at least the same non-rounded shape in cross-section and the same increased diameter at its ends. This can best be seen in FIG. 7 and FIG. 4 with reference number 161. It fixes the rod more securely within the hole. This rod is preferably the connecting rod 2.

A second fixation opening 18 is arranged in the top 13, extending through the main body to the second hole 16 and is crossing it. The second fixation opening 18 has an internal thread 180 as well. It has preferably the same size as the first fixation opening 17 and it serves also to hold a second fixation screw 181.

As can be best seen in FIG. 8, the first hole 15 and the second hole 16 do not penetrate each other. Preferably, they extend in two parallel planes, their first and second central axis 150, 160 being perpendicular, but spaced from each other.

Figure 9:
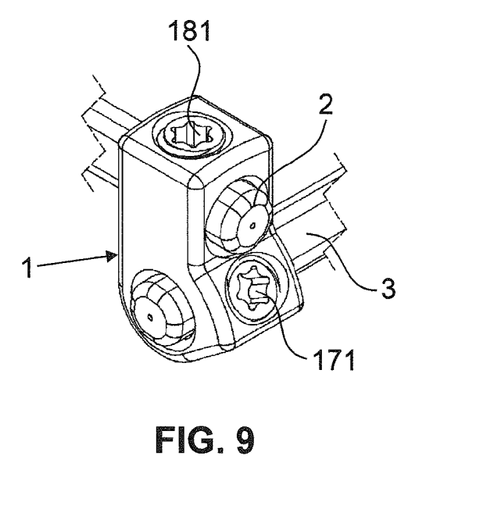
FIG. 9 a first perspective view of an iliac connector according to the invention with a spinal rod arranged in the connector.
Figure 10:
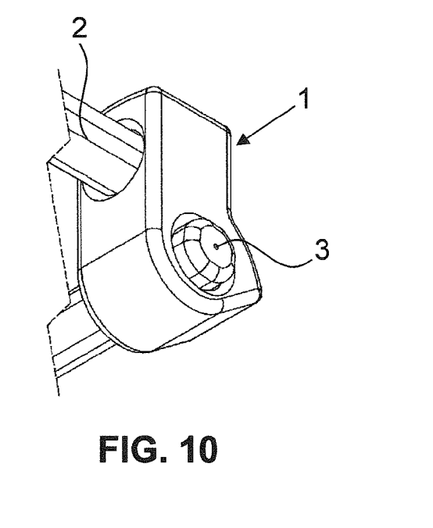
FIG. 10 a second perspective view of the iliac connector according to FIG. 9.
Figure 11:
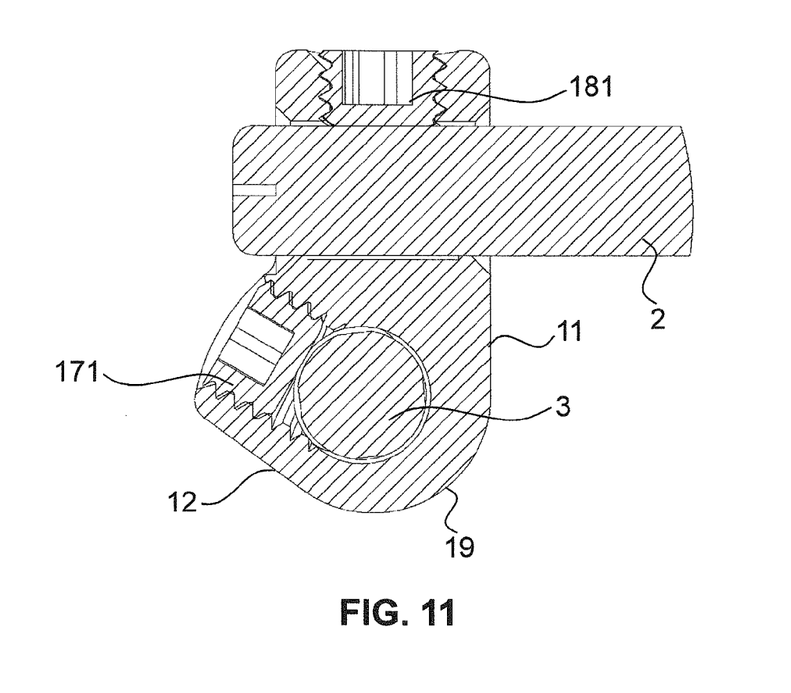
FIG. 11 a longitudinal section of the iliac connector according to FIG. 9.

FIGS. 9 to 11 show the connector head 1 in use with the inventive connecting rod 2 and the spinal rod 3. As can be seen, each rod 2, 3, is fixed independently from each other by the first fixation screw 171 and the second fixation screw 181 respectively. Preferably, both rods 2, 3 penetrate the holes 15, 16, their ends protruding the head 1. As can be seen in FIGS. 1 and 9, the screws 171 and 181 can be fixed independently from each other and in a freely chosen chronological order.

FIGS. 12 to 20 show a second embodiment of the inventive spinal fixation system and second embodiments of connector heads. While the connector head of the first embodiment is symmetrically built and the same shape of connector head can be used on both sides of the spine, the system according to this second embodiment comprises a left side and a right side connector head, the two heads being mirrored.

Figures 12, 13:
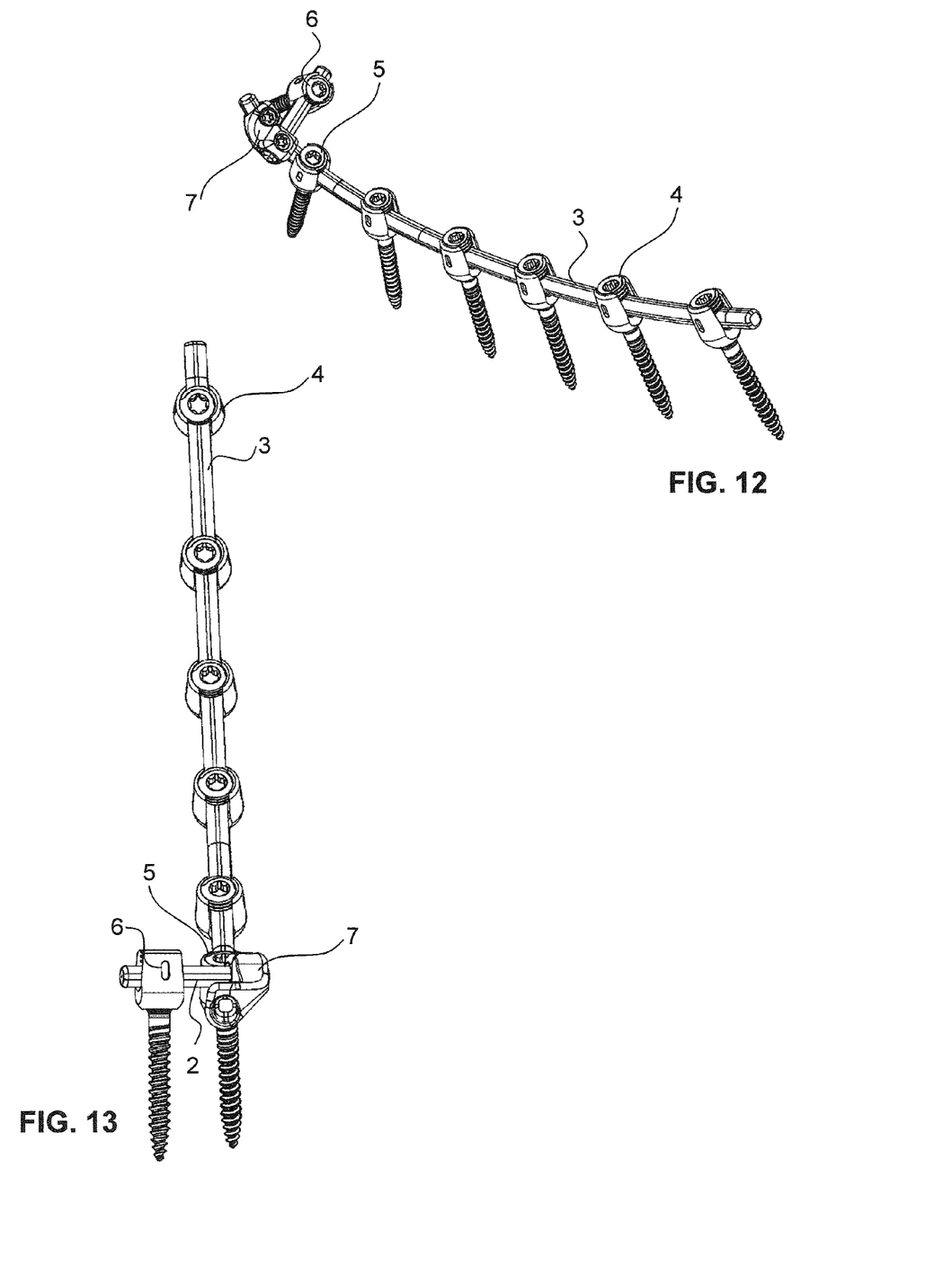
FIG. 12 a spinal fixation system according to a second embodiment of the invention, in a first perspective view.
FIG. 13 the fixation system according to FIG. 12 in a second perspective view.

As can be seen in FIGS. 12 and 13, the only difference of the spinal system according to the first and this second embodiment is the different kind of connector head used. This head bears in this second embodiment the reference numbers 7, 7' (see FIG. 15). The other elements remain unchanged, and there reference numbers are identical with the ones of the first embodiment. The description of these elements, already mentioned above, is therefore also applicable to this embodiment.

Figure 14:
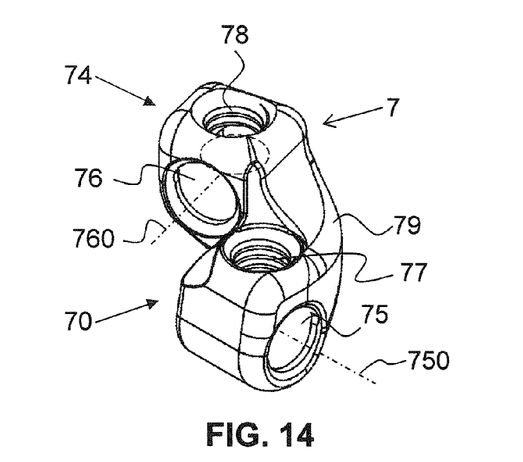
FIG. 14 a left side connector head according of the spinal fixation system according to FIG. 12 in a perspective view.
Figure 15:
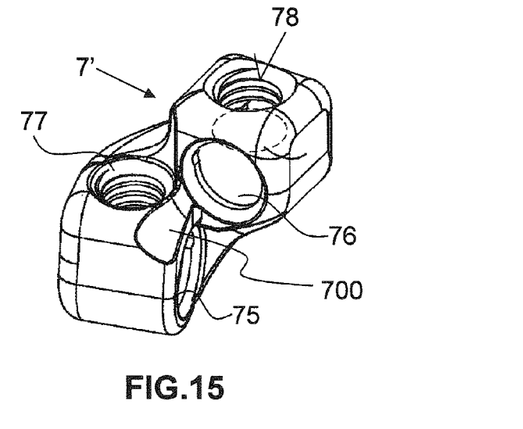
FIG. 15 a perspective view of a right side connector head for use in a spinal fixation system.
Figure 16:
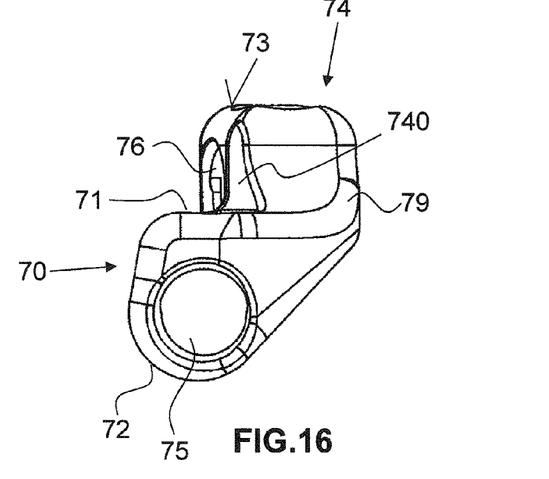
FIG. 16 a rear view of the left side connector head according to FIG. 14.
Figure 17:
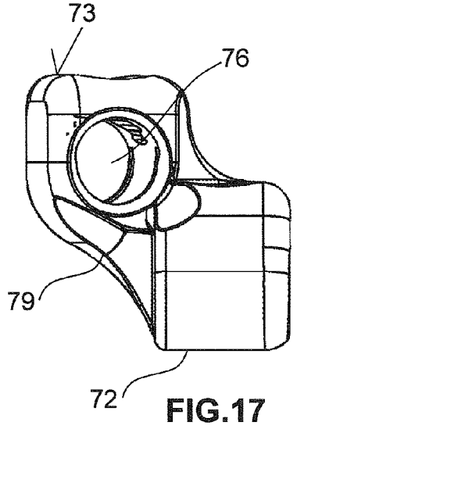
FIG. 17 a side view of the left side connector head according to FIG. 14.
Figure 18:
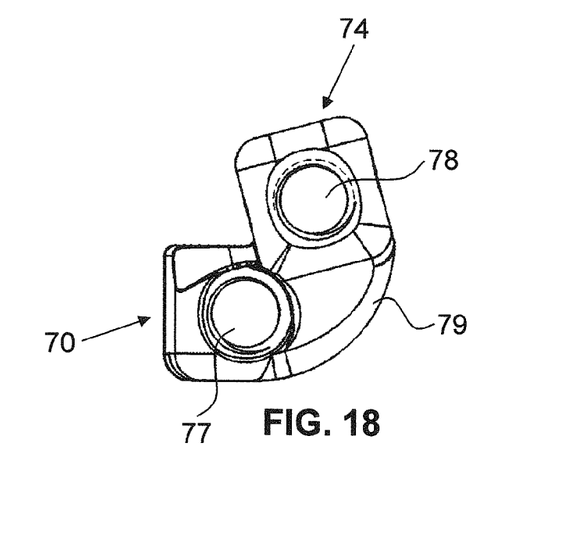
FIG. 18 a top view of the left side connector head according to FIG. 14.
Figure 19:
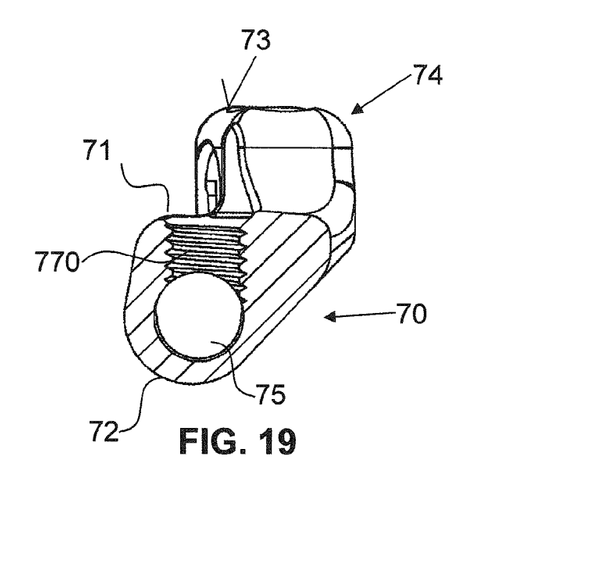
FIG. 19 a first longitudinal section view of the connector head according to FIG. 14 and FIG. 20 a second longitudinal section view of the connector head according to FIG. 14.
Figure 20:
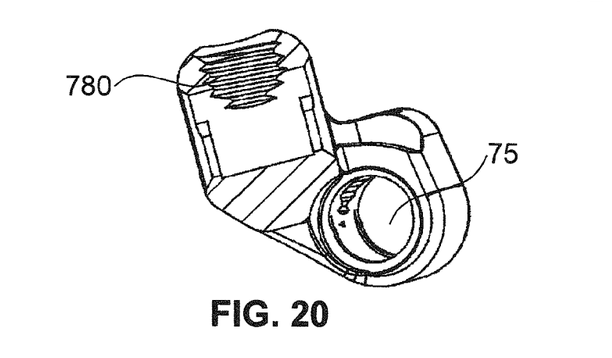

FIG. 14 shows a left side connector head 7, which can be used in the system according to FIGS. 12 and 13, i.e. on the left side of the spine. FIG. 15 shows a right side connector head 7', which can be used with a similar or identical system on the right side of the spine. As can be seen in comparison of FIGS. 14 and 15, the right side connector head 7' is the mirror picture of the left side connector head 7. In the following, only the left side connector head 7 will be described. However, the same description also applies to the right side connector head 7'.

The connector head 7 of FIG. 14 is made of one single piece as a unitary part. Preferably it is made of the same material as the screws 4 mentioned above, for example it is made of titanium. The left side and the right side connector heads 7, 7' are similar to the one shown in FIGS. 1 to 11. The previous description of this connector head 1 according to the first embodiment is therefore applicable to these connector heads 7, 7' as well, where appropriate. Identical or similar features, especially the ones shown in the figures, will not be described in detail any more.

The connector head 7 comprises a first body 70 and a second body 74. The first body 70 is also called spinal body and the second body is also called connecting body. Both bodies 70, 74 have preferably a cube-like shape. A transition area 79 is connecting the two bodies 70, 74 with each other. The transition area 79 is preferably rounded, as can be best seen in FIG. 18. The transition area 79 has a twisted shape, as can be best seen in FIG. 14.

The edges of the two bodies 70, 74 are preferably rounded as well. The bottom 72 of the connector head 7, which is preferably the bottom of the first body 70, can be rounded as well. These rounded parts ensure, that no human tissue gets hurt.

The first body 70 comprises the first hole 75 and the first fixation opening 77. The second body 74 comprises the second hole 76 and the second fixation opening 78. At least one, preferably both holes 75, 76 are through holes. The fixations openings 77, 78 comprise preferably threads 770, 780, as can be best seen in FIGS. 19 and 20.

The first hole 75 comprises a first central axis 750 and the second hole 76 comprises a second central axis 760, wherein these axis extend perpendicular but at a distance to each other; i.e. they do not cross each other and are therefore extending in planes different from each other.

The first body 70 is arranged below and staggered to the second body 74. They are like steps of a circular staircase. The top surface 71 of the first body 70 extends preferably parallel to the top surface 73 of the second body 74, but at a distance below it, as can be best seen in FIGS. 16 and 17. The first fixation opening 77 is arranged in the top surface 71 of the first body 70 and the second fixation opening 78 is arranged in the top surface 73 of the second body 74. This means that their threads 770, 780 extend in the same direction, perpendicular to the central axis 750, 760 of the first and second holes 75, 76.

The first body 70 comprises a recess 700 which extends in direction of the second central axis 760 from the second hole 76 to the opposite end of the first body. This recess 700 has a rounded cross-section suitable to accommodate the connecting rod 2.

The second body 74 comprises a recess 740 which extend from the first fixation opening 77 to the top surface 73 of the second body. This recess 740 optimizes the access to the first fixation opening 77, so that a screw can be easily entered and fixed into this first fixation opening 77.

As can be seen in FIGS. 12 and 13, this connector head 7, 7' minimizes the space needed for the connection of a connecting rod 2 and a spinal rod 3, but gives still independent access to both holes 75, 76 and to both fixation openings 77, 78.

The inventive iliac connector enables a stabilization of ilium, sacrum and spine and allows at the same time movements between ilium and sacrum.

| LIST OF REFERENCE SIGNS | |
|---|---|
| 1 | connector head |
| 10 | side wall |
| 11 | rear wall |
| 12 | bottom |
| 13 | top |

-continued

LIST OF REFERENCE SIGNS

| | |
|---|---|
| 14 | front wall |
| 140 | flat section |
| 141 | inclined section |
| 15 | first hole |
| 150 | first central axis |
| 151 | non-rounded part |
| 16 | second hole |
| 160 | second central axis |
| 161 | non-rounded part |
| 17 | first fixation opening |
| 170 | first thread |
| 171 | first fixation screw |
| 18 | second fixation opening |
| 180 | second thread |
| 181 | second fixation screw |
| 19 | transition area |
| 2 | connecting rod |
| 3 | spinal rod |
| 4 | spinal bone screw |
| 5 | sacral bone screw |
| 6 | iliac bone screw |
| 7 | connector head |
| 7' | connector head |
| 70 | first body (spinal body) |
| 700 | first recess |
| 71 | first top surface |
| 72 | bottom |
| 73 | second top surface |
| 74 | second body (connecting body) |
| 740 | second recess |
| 75 | first hole |
| 750 | first central axis |
| 76 | second hole |
| 760 | second central axis |
| 77 | first fixation opening |
| 770 | first thread |
| 78 | second fixation opening |
| 780 | second thread |
| 79 | transition area |
| α | angle |
| SP | Spine |
| I | Ilium |
| S | Sacrum |

The invention claimed is:

1. An iliac connector comprising a connector head and an elongate connecting member for connecting a sacrum or a spine to an ilium,
the connector head having a first hole for receiving an elongate spinal member, the elongate spinal member penetrating at least one spinal bone screw, and
the connector head having a second hole for receiving the elongate connecting member, the elongate connecting member being held in at least one iliac bone screw,
wherein the first hole has a first central axis and the second hole has a second central axis, wherein first central axis extends in a first direction and the second central axis extends in a second direction, wherein the first direction is different to the second direction and wherein the first direction and the second direction are at an angle to each other,
wherein the connector head further has a first fixation opening for holding a first fixation screw and a second fixation opening for holding a second fixation screw,
the first fixation opening leading to the first hole to hold the elongate spinal member received in the first hole with the first fixation screw and the second fixation opening leading to the second hole to hold the elongate spinal member received in the second hole with the second fixation screw,
wherein the first fixation opening has a third central axis extending perpendicular to the first central axis of the first hole and the second fixation opening has a fourth central axis extending perpendicular to the second central axis of the second hole, and
wherein the elongate connecting member is made of a material being more flexible than titanium.

2. The iliac connector according to claim 1, wherein the elongate connecting member is made of filament composite material, wherein the filaments are oriented in an axial direction of the elongate connecting member.

3. The iliac connector according to claim 2, wherein the filaments are carbon filaments encapsulated in a polymer matrix, preferably polyether-ketoneetherketoneketone (PEKEKK) or polyetheretherketone (PEEK).

4. The iliac connector according to claim 1, wherein the elongate connecting member has throughout its whole length a non-changing cross-section.

5. The iliac connector according to claim 1, wherein the elongate connecting member is a rod.

6. The iliac connector of claim 1 wherein the second axis is extending at an angle of 84° to the first central axis.

7. The iliac connector of claim 1 wherein the second axis is extending at an angle of 90° to the first central axis.

8. The iliac connector of claim 1, wherein the third central axis and the fourth central axis extend parallel to one other.

9. A connector head for use in an iliac connector according to claim 1, wherein the connector head has a first hole having a first central axis for receiving an elongate spinal member and a second hole having a central second axis for receiving an elongate connecting member, wherein the connector head further has a first fixation opening for holding a first fixation screw and a second fixation opening for holding a second fixation screw, wherein the first fixation opening has a third central axis extending perpendicular to the first central axis of the first hole and the second fixation opening has a fourth central axis extending perpendicular to the second central axis of the second hole, wherein the first central axis and the second central axis extend perpendicular to one another, wherein the first hole is in communication with the first fixation opening and the second hole is in communication with the second fixation opening, the first and second fixation openings being arranged such they allow mounting of the elongate connecting member and the elongate spinal member independently from each other.

10. The connector head of claim 9, wherein the fixation opening of the first hole is arranged at an angle different from 90° to the fixation opening of the second hole.

11. The connector head of claim 10, wherein the angle is between 70° to 30°.

12. The connector head of claim 10, wherein the angle is between 60° to 40°.

13. The connector head of claim 10, wherein the angle is about 60° or 45° or less than 45°.

14. The connector head of claim 10, wherein the angle is approximately 0°.

15. The connector head of claim 6, wherein the connector head comprises two side walls, a rear wall, a front wall, a bottom and a top, wherein the first hole is arranged at least in one of the side walls, the second hole is arranged at least in the rear wall, the first fixation opening is arranged in the front wall and the second fixation opening is arranged in the top.

16. The connector head of claim 15, wherein the front wall comprises at least one section which is inclined with respect to the rear wall and wherein the first fixation opening is arranged in the inclined section.

17. The connector head of claim 15, wherein a transition area connects the rear wall and the bottom and wherein this transition area is rounded.

18. The connector head of claim 9, wherein the first fixation opening is arranged in a first surface of the connector head and the second fixation opening is arranged in a second surface of the connector head, wherein the first surface extends in a plane parallel but at a distance to a plane defined by the second surface.

19. The connector head of claim 9, wherein the connector head comprises a first body with a cube-like shape and a second body with a cube-like shape, the first body comprising the first hole and the first fixation opening and the second body comprising the second hole and the second fixation opening, wherein the first body is arranged staggered below the second body.

20. The connector head of claim 9, wherein and least one of the first and the second hole is a through hole.

21. A spinal fixation system comprising:
an iliac connector, the iliac connector comprising a connector head and an elongate connecting member for connecting a sacrum or a spine to an ilium,
the connector head having a first hole for receiving an elongate spinal member, the elongate spinal member penetrating at least one spinal bone screw, and the connector head having a second hole for receiving the elongate connecting member, the elongate connecting member being held in at least one iliac bone screw, the first hole having a first central axis and the second hole having a second central axis,
wherein the first central axis extends in a first direction and the second central axis extends in a second direction, wherein the first direction is different to the second direction and wherein the first direction and the second direction are at an angle to each other,
wherein the connector head further has a first fixation opening for holding a first fixation screw and a second fixation opening for holding a second fixation screw, wherein the fixation system comprises the first and the second fixation screw, the first fixation opening leading to the first hole to hold the elongate spinal member received in the first hole with the first fixation screw and the second fixation opening leading to the second hole to hold the elongate spinal member received in the second hole with the second fixation screw,
wherein the fixation system comprises the first and the second fixation screw,
wherein the first fixation opening has a third central axis extending perpendicular to the first central axis of the first hole and the second fixation opening has a fourth central axis extending perpendicular to the second central axis of the second hole,
wherein the elongate connecting member is made of a material being more flexible than titanium,
wherein at least one of the at least one spinal bone screw and at least one sacral bone screw hold the elongate spinal member, wherein the elongate spinal member is held in the connector head of the iliac connector,
wherein the elongate connecting member of the iliac connector is held in the at least one iliac bone screw, and
wherein the system stabilizes spine and ilium thereby allowing some movement between ilium and sacrum.

22. The spinal fixation system of claim 21 wherein the wherein the elongate connecting member and the elongate spinal member are made of a filament composite material, wherein the filaments of the elongate connecting member are oriented in an axial direction of the elongate connecting member and wherein the filaments of the elongate spinal member are oriented in an axial direction of the elongate spinal member, so that the filaments of the elongate spinal member are oriented at an angle to the filaments of the elongate connecting member.

23. The spinal fixation system of claim 22, wherein the filaments are carbon filaments encapsulated in a polymer matrix, preferably polyether-ketoneetherketoneketone (PEKEKK) or polyetheretherketone (PEEK).

24. The spinal fixation system according to claim 21, wherein the elongate spinal member and the elongate connecting member are made of the same material.

25. The spinal fixation system according to claim 21, wherein at least one of, preferably both, the elongate spinal member and the elongate connecting member is a rod.

26. The spinal fixation system of claim 21 wherein the second axis is extending at an angle of 84° to the first central axis.

27. The spinal fixation system of claim 21 wherein the second axis is extending at an angle of 90° to the first central axis.

28. The spinal fixation system of claim 21, wherein the third central axis and the fourth central axis extend parallel to one other.

* * * * *

UNITED STATES PATENT AND TRADEMARK OFFICE
CERTIFICATE OF CORRECTION

PATENT NO. : 9,561,058 B2
APPLICATION NO. : 13/890822
DATED : February 7, 2017
INVENTOR(S) : Robert Lange et al.

Page 1 of 1

It is certified that error appears in the above-identified patent and that said Letters Patent is hereby corrected as shown below:

In the Claims

At Claim 1, Column 11, Line 53, after "wherein" and before "first" should be --the--.
At Claim 1, Column 11, Line 66, delete "spinal" and insert --connecting--.
At Claim 21, Column 13, Line 44, delete "spinal" and insert --connecting--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*